(12) United States Patent
Garner et al.

(10) Patent No.: US 7,454,939 B2
(45) Date of Patent: Nov. 25, 2008

(54) INSTRUMENT FOR BENDING SPINAL RODS USED IN A SPINAL FIXATION SYSTEM

(75) Inventors: Ronald Garner, Hull, MA (US); Thomas J. Runco, Canton, MA (US)

(73) Assignee: DePuy Spine, Inc., Raynham, MA (US)

( * ) Notice: Subject to any disclaimer, the term of this patent is extended or adjusted under 35 U.S.C. 154(b) by 596 days.

(21) Appl. No.: 11/035,235

(22) Filed: Jan. 12, 2005

(65) Prior Publication Data

US 2006/0150698 A1 Jul. 13, 2006

(51) Int. Cl.
*B21D 7/02* (2006.01)
*B21D 7/024* (2006.01)

(52) U.S. Cl. .............................. 72/218; 72/387; 72/458; 72/479

(58) Field of Classification Search .................... 72/213, 72/216, 217, 332, 334, 389.1, 308, 387, 390.4, 72/390.5, 409.13, 413, 458, 459, 218, 156
See application file for complete search history.

(56) References Cited

U.S. PATENT DOCUMENTS

| | | | | |
|---|---|---|---|---|
| 2,502,713 A | * | 4/1950 | Fagge | 72/388 |
| 3,808,867 A | * | 5/1974 | Becker | 72/321 |
| 4,077,249 A | * | 3/1978 | Schmitter | 72/390.2 |
| 4,887,447 A | * | 12/1989 | Schweitzer | 72/332 |
| 5,113,685 A | * | 5/1992 | Asher et al. | 72/458 |
| 5,651,283 A | | 7/1997 | Runciman et al. | |
| 5,819,580 A | * | 10/1998 | Gauthier | 72/458 |
| 6,006,581 A | | 12/1999 | Holmes | |
| 6,035,691 A | * | 3/2000 | Lin et al. | 72/413 |
| 6,644,087 B1 | * | 11/2003 | Ralph et al. | 72/213 |

\* cited by examiner

*Primary Examiner*—David B Jones
(74) *Attorney, Agent, or Firm*—Lahive & Cockfield, LLP; Kevin J. Canning

(57) ABSTRACT

An instrument and method for bending a surgical implant, such as a spinal rod, includes a lever pivotally connected to a handle through a movable linkage system. The movable linkage system includes one or more bearing surfaces for applying a force to a first portion of the surgical implant while a rod seat connected to the handle holds an adjacent second portion of the surgical implant in a fixed position, thereby causing the surgical implant to bend between the first and second portion. The instrument can be easily operated using a single hand, is easy to control and requires a relatively small amount of force to bend a surgical implant. The instrument can include an automatic advancement means for advancing the surgical implant after bending to bend another portion of the surgical implant by a selected amount. The instrument can also be used for bending spinal rods having a non-circular cross-section in multiple planes.

19 Claims, 9 Drawing Sheets

INSTRUMENT FOR BENDING SPINAL RODS USED IN A SPINAL FIXATION SYSTEM

RELATED APPLICATIONS

The present invention relates to U.S. patent application Ser. No. 11/035,282 entitled "Instrument for Bending Spinal Rods Used in a Spinal Fixation System", filed on even date herewith.

FIELD OF THE INVENTION

The present invention relates to spinal fixation systems used in orthopedic surgery to align, adjust and/or fix portions of the spinal column. More particularly, the present invention relates to an instrument for bending a spinal rod used in a spinal fixation system to conform to a desired curvature of the spinal column in one or more anatomic planes.

BACKGROUND OF THE INVENTION

Spinal fixation systems may be used in surgery to align, adjust and/or fix portions of the spinal column, i.e., vertebrae, in a desired spatial relationship relative to each other. Many spinal fixation systems employ a spinal rod for supporting the spine and for properly positioning components of the spine for various treatment purposes. The spinal rods, which are generally formed of a metal, such as stainless steel or titanium, may be implanted to correct deformities, prevent movement of vertebral bodies relative to each other or for other purposes. Vertebral anchors, comprising pins, bolts, screws, and hooks, engage the vertebrae and connect the supporting rod to different vertebrae.

Spinal support rods frequently oriented at various angles and positions due to the anatomical structure of the patient, the physiological problem being treated, and the preference of the physician. The size, length and bend of each spinal rod depend on the size, number and position of the vertebrae to be held in a desired spatial relationship relative to each other by the apparatus, which is generally different for each patient. A rod may be bent, as desired, to conform to a desired curvature of the spinal column in one or more of the anatomic planes, in order to fit the rod into the vertebral anchors.

In the current state of the art, bending of spinal rods is typically accomplished using a hand-operated instrument, commonly known as a "French bender". The French bender is a pliers-like instrument that requires both hands to operate and provides no additional leverage beyond that achieved by the length of the handle. Because spinal rods are formed of materials that are not easily bendable, such as titanium, a significant amount of force is required to bend the rods. French benders and other known instruments for bending spinal rods are also difficult to control for producing accurate and reproducible curves. In addition, the "French bender" is generally only configured to receive rods having a circular cross-section and cannot easily bend rods having a non-circular cross-section.

SUMMARY OF THE INVENTION

The present invention provides an improved instrument and method for bending a spinal rod or other surgical implant to conform to a desired form, for example, the curvature of the spinal column in one or more anatomic planes. The instrument for bending a spinal rod includes a lever pivotally connected to a handle through a movable linkage system. The movable linkage system includes one or more bearing surfaces for applying a force to a first portion of the rod while a rod seat connected to the handle holds an adjacent second portion of the rod in a fixed position, thereby causing the rod to bend between the first and second portion. The instrument can be easily operated using a single hand, is easy to control and requires a relatively small amount of force to bend a rod. The instrument can include an automatic advancement means, such as a ratchet, pawl or frictional latch, for advancing the rod after bending to bend another portion of the rod by a selected amount. The instrument can also be used for bending rods having a non-circular cross-section in multiple planes.

According to one aspect of the invention, an instrument for bending a surgical implant is provided. The instrument comprises a handle, a lever pivotally connected to the handle, and a movable linkage system. The movable linkage system includes a plurality of pivotally connected links for pivotally connecting the lever to the handle. One of the pivotally connected links of the movable linkage system applies a force to the surgical implant to bend the second portion relative to the first portion upon pivoting the lever relative to the handle.

According to another aspect of the invention, an instrument for bending a surgical implant is provided, comprising a handle, a lever pivotally connected to the handle and a movable linkage system. The movable linkage system pivotally connects the lever to the handle and applies a force to bend a first portion of the surgical implant relative to a second portion of the surgical implant upon pivoting the lever relative to the handle. The instrument further includes an advancement mechanism for automatically moving the surgical implant relative to the instrument upon pivoting of the lever relative to the handle.

According to still another aspect of the invention, an instrument for bending a surgical implant comprises a handle, a lever pivotally connected to the handle, and a rotatable insert coupled to the handle for seating the surgical implant. The rotatable insert applies a force to bend the surgical implant upon pivoting of the lever towards the handle. The rotatable insert may accommodate rods having non-circular geometries.

According to yet another aspect of the invention, an instrument for bending a spinal rod to replicate a curvature of a spine is provided. The instrument comprises a handle having a first end and a second end, a rod seat connected to the first end of the handle for receiving a first portion of the spinal rod, a bending roller coupled to the rod seat and defining a top portion of the rod seat, a lever pivotally connected to the handle at a pivot point between the first end and the second end of the handle, and a movable linkage system coupled to a first end of the lever. The pivot point of the lever is located between the first end and a second end of the lever. The movable linkage system is also coupled to the bending roller for applying a force to a second portion of the rod to bend the second portion of the rod relative to the first portion upon moving of the second end of the lever towards the second end of the handle.

According to another aspect of the invention, a method of bending a spinal rod comprises the steps of inserting a first portion of a spinal rod into a first channel of an instrument for bending a spinal rod and a second portion of the spinal rod into a second channel of the instrument and pivoting a first end of a lever of the instrument towards a first end of the handle of the instrument. The step of pivoting the first end of the lever pivots the first channel relative to the second channel in a second direction away from the handle, creating a bend in the rod between the first portion and the second portion.

According to yet another aspect of the invention, a method of bending a spinal rod comprises the steps of inserting the spinal rod into an instrument for bending a spinal rod and moving a lever of the instrument towards a handle of the instrument to cause a link of a movable linkage system to pivot, thereby applying a bending force to the rod.

According to a final aspect of the invention, a method of bending a spinal rod is provided, which comprises the steps of inserting the spinal rod into an instrument for bending a spinal rod, moving a lever of the instrument towards a handle of the instrument to create a first bend in the spinal rod simultaneously advancing the rod relative to the instrument, and releasing the lever to hold the rod in a forward position. The method further comprises the step of moving the lever of the instrument towards the handle to create a second bend in the spinal rod.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

DETAILED DESCRIPTION OF THE INVENTION

Figure 1A:
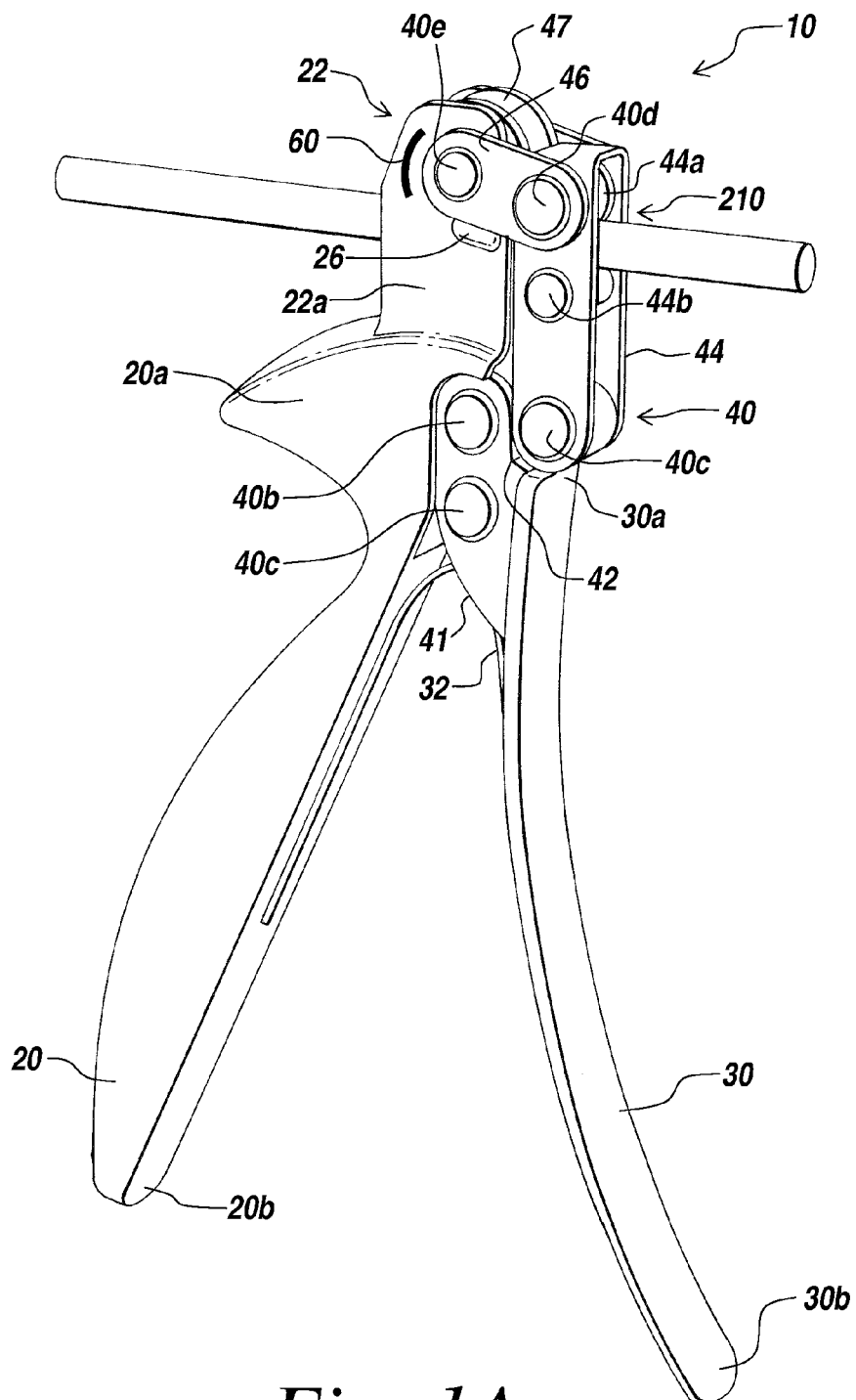
FIG. 1A is a front perspective view of an instrument for bending a spinal rod according to an illustrative embodiment of the invention.

The present invention provides an improved instrument for bending a component of a spinal fixation system, such as a surgically implantable spinal rod. The illustrative instrument can be used to bend, straighten, adjust or otherwise change the bend of a spinal rod using less manual force than prior rod bending systems. The present invention will be described below relative to an illustrative embodiment. Those skilled in the art will appreciate that the present invention may be implemented in a number of different applications and embodiments and is not specifically limited in its application to the particular embodiments depicted herein.

The terms "upper", "top", "lower", "bottom", "forward", "front", "rearward" and "back" are relative terms used to describe the position and orientation of different components of the instrument relative to each other, and are not intended to limit the invention in any way.

Referring to FIGS. 1A-1E, a rod-bending instrument 10 of an illustrative embodiment of the invention facilitates bending of a component of a spinal fixation system, such as a spinal rod, into a desired form by utilizing an ergonomically advantageous design. The invention will be described for use with a spinal rod, though one skilled in the art will recognize that the instrument 10 can be used to bend any surgical component. The illustrative instrument 10 provides compound leverage to reduce the force required to bend the rod, allowing for greater accuracy and reduced fatigue. In an illustrative embodiment, the rod-bending instrument 10 can be operated using one hand, which facilitates use of the instrument.

The rod-bending instrument 10 includes a handle portion 20 configured to fit in the palm of a user of the instrument 10 and a lever portion 30 pivotally coupled to the handle portion 20. As shown, the handle portion 20 provides an ergonomically acceptable grip and further includes a rod seat 22 connected to an upper end 20a of the handle portion 20. The rod seat 22 includes two side walls 22a, 22b forming a channel 220 configured to receive and hold a rod to be bent using the instrument 10. The top portion of the channel 220 may be defined in part by a bending roller 47 extending between the side walls 22a, 22b. As used herein, the term "channel" refers to any structure for defining a path for seating at least a portion of a surgical implant, and is not limited to a cylindrical-shaped pathway. Rather, the channel of the rod seat can have any suitable size, shape, orientation and configuration suitable for receiving at least a portion of a surgical implant.

In the illustrative embodiment, the rod extends substantially perpendicular to the handle portion 20 when seated in the rod seat 22, though one skilled in the art will recognize that the rod seat 22 may be configured to hold the rod in any suitable orientation relative to the handle.

The instrument 10 further includes a moveable linkage system 40 for rotatably coupling the lever portion 30 to the handle portion 20 and for applying a force to bend the rod when the lever portion 30 pivots toward the handle portion 20. A user actuates the instrument 10 to provide controlled bending of a rod inserted in the rod seat 22 by pivoting the lower end 30a of the lever portion 30 toward the handle portion 20, for example, by squeezing the lever 30 while holding the handle 20. As the lever portion 30 pivots toward the handle portion 20, the moveable linkable system 40 applies a force to a selected portion of the rod to bend the rod in the vicinity of the selected portion by a predetermined amount, as described in detail below.

A biasing mechanism, illustrated as a spring 32, may be provided between the handle portion 20 and the lever portion 30 for biasing the lever portion 30 toward a selected position. In the embodiment shown in FIGS. 1A-1B, the spring 32 biases the lever portion 30 away from the handle 20 towards a rest position, in which no force is applied to a rod seated in the rod seat. One skilled in the art will recognize that any suitable means may be used to bias the lever portion 30 and/or the handle portion toward a selected position.

The movable linkage system 40 translates movement of the lever 30 into bending of a rod or other component held by the rod seat 22. The movable linkage system 40 of the illustrative embodiment includes a plurality of pivotally connected links that translate movement of the lever 30 towards the handle into an upward and forward force applied to the rod. The kinematics of the linkage system 40 give a mechanical advantage to the user, allowing for the movement of the lever 30 to produce a force sufficient to bend a rod. The components of the movable linkage system include a lever pivot 41 connected to the upper end 30a of the lever 30, a compound lever link 42 pivotally coupled to the lever pivot 41, a strap 44 pivotally connected to the compound lever link 42 and a top link 46 pivotally connected to the strap 44 for constraining the movement of the strap 44. The top link 46 is pivotally connected to the side walls 22a, 22b of the rod seat 22 above the channel 220. The components of the movable linkage system 40 cooperate to cause controlled bending of a portion of a rod when the user selectively moves the lever 30.

As shown in FIGS. 4A-4E, pins 40a-40e form hinge points for pivotally connecting the different links of the movable linkage system. A first pin 40a forms a first hinge point for pivotally connecting the handle portion 20 to the lower end 41b of the lever pivot 41. The lever pivot 41, the lower end 41b of which is rigidly coupled to or integral with an upper end 30b of the lever 30, extends substantially parallel to and opposite the lever 30 relative to the first hinge point 40a. Rotation of the lower end 30a of the lever 30 toward the handle 20 about the first hinge point causes the upper end 41a of the lever pivot 41 opposite the first hinge point to move away from the handle. A second pin 40b pivotally connects the upper end 40a of the lever pivot 41 to a back end 42b compound lever link 42 at a second hinge point. The second hinge point is preferably located between the first hinge point 40a and the rod seat 22, towards the upper end of the lever pivot 41. The compound lever link 42 extends perpendicular to the lever pivot 41 and substantially parallel to the channel 220 for seating the rod, to connect the lever pivot 41 to the strap 44, which extends substantially parallel to the lever pivot 41 when the instrument 10 is in a rest position. A third hinge point, about pin 40c, pivotally connects the second, forward end 42a of the compound lever link 42 to a first, lower end 44b of the strap 44. A fourth pin 40d pivotally connects the second, upper end 44a of the strap on the opposite side of the rod seat channel 220 from the third pin 40c. The top link 46 extends substantially perpendicular to the strap 44 for connecting the strap 44 to the rod support 22. A fifth pin 40e pivotally connects the second end of the top link 46 to the rod seat 22. The bending roller 47 is preferably concentric with the fifth pin 40e, which can also secure the bending roller 47 in place, in addition to pivotally connecting the top link 46 to the rod seat. One skilled in the art will recognize that any suitable means for pivotally connecting the links of the moveable linkage system 40 may be used in accordance with the teachings of the invention.

The strap 44 spans the channel 220 and includes two rollers 44a, 44b, or otherwise fixed points, located adjacent to and forward from the rod seat 22. The rollers 44a, 44b cooperate to define a channel 210 in communication with the rod seat channel 220 for receiving a forward portion of the rod therebetween. In the illustrative embodiment, the center of the top roller 44a is concentric with and secured by the pin 40d coupling the strap 44 and the top link 46. For example, the pin 40d can be inserted through the top roller 44a, such that the axis of rotation of the strap 44 relative to the top link 46 aligns with the axis of the top roller 44a. When the instrument 10 is in a rest position, the channel 210 defined by the rollers 44a, 44b has an inner diameter that substantially matches the outer diameter of the rod to be bent using the instrument. In the rest position, the channel 210 between the rollers 44a, 44b substantially aligns with the rod seat, such that a rod inserted in the rod seat channel 220 extends straight between the rollers 44a, 44b.

The strap rollers 44a, 44b and the bending roller 47 define bearing surfaces for selectively applying a force to the rod 50 to bend the forward portion of the rod in the channel 210 relative to the rear portion of the rod inserted the rod seat channel 220. When a user actuates the instrument by squeezing handle 20 and lever 30, the movable linkage system 40 pivots the channel 210 defined between the rollers 44a, 44b, relative to the rod seat channel defined by the bending roller 47, while applying force to the from the bearing surfaces. During actuation, the rollers 44a, 44b lock the rod to the strap 44 and push the front portion of the rod forward and upwards from the rod seat 22, while the bending roller 47 retains the rear portion of the rod. As a result, the rod is forced against and drawn along the bending roller 47 producing a fair bend along a selected plane in the rod, as described in detail below.

A biasing spring (not shown) can also be provided for returning the strap 44 to a rest position after bending.

The housing 20 can also include a stop 26 for constraining the movement of the top link. In the embodiment shown in FIGS. 1A-1E, the stop 26 comprises a protrusion on an outer surface of one of the side walls of the rod seat 22 configured to abut the top link 26, preventing the top link from rotating below the stop. The stop 26 thus holds the strap 44 in a perpendicular position when the instrument is at rest, such that the channel 210 between the rollers 44a, 44b aligns with the rod seat channel 220. According to one embodiment, a lock can be provided to prevent the top link 46 from moving up relative to the rod seat 22. The lock would allow for a relatively sharper bend or kink in the rod to be made.

According to one embodiment of the invention, the instrument 10 can further includes a rod advancer 60 for selectively advancing the rod relative to the instrument 10. The illustrative rod advancer 60 advances the rod through the channels 210, 220 by a predetermined amount to allow the user to select the portion of the rod to be bent. The rod advancer 60 can comprise a gear and ratchet coupled to the bending roller 47, a ratchet, pawl, frictional latch or any suitable means known in the art. For example, the primary means for advancing the rod may be the action of the linkage system 40, whereby the top and bottom rollers 44a, 44b, respectively, of the strap apply a bending force and impart a forward motion along the rod. When the lever 30 is released, the rollers return to their original position. However, frictional forces within the linkage and roller system 40 may prevent the rod from moving backwards.

Figure 2:
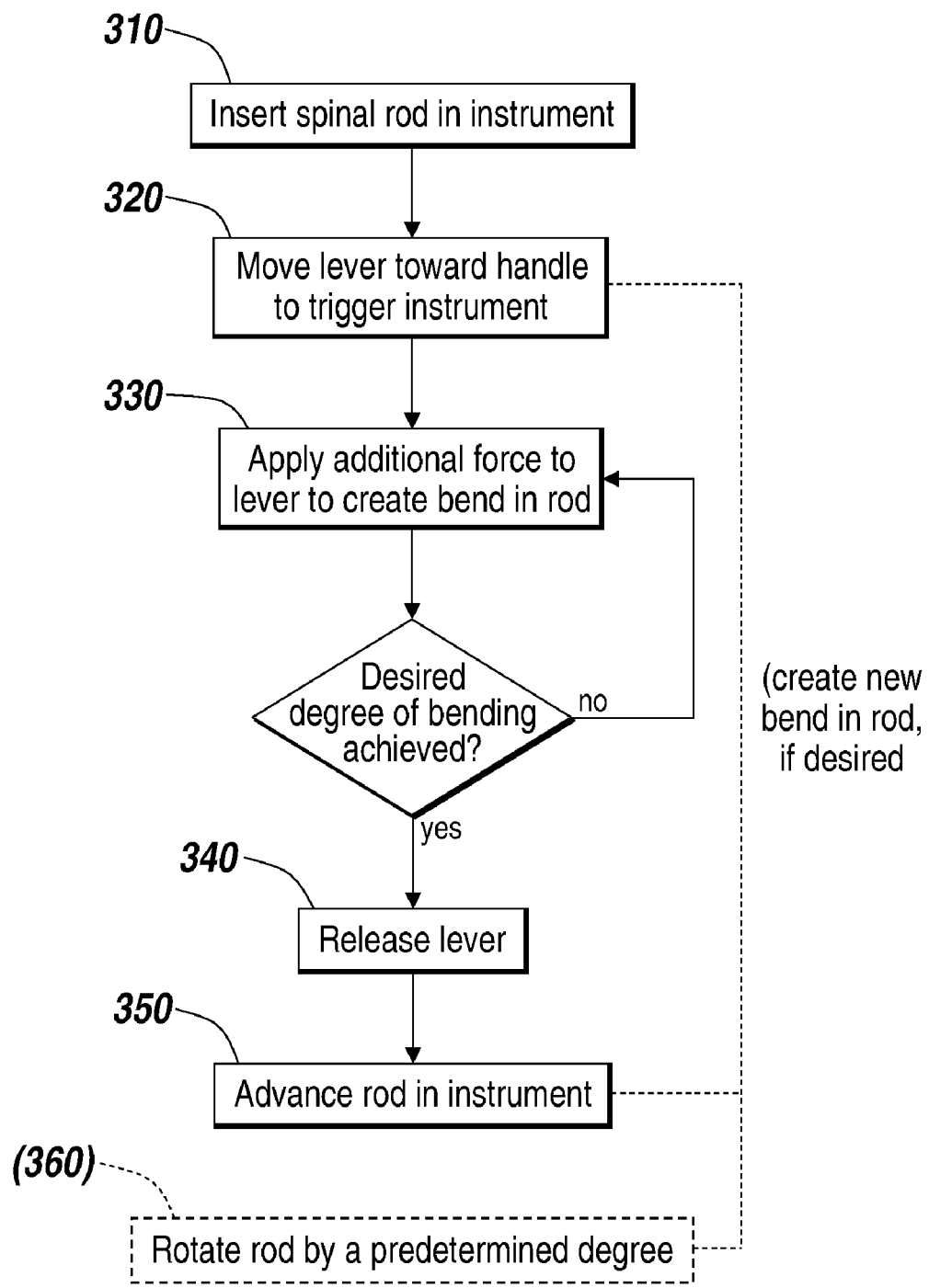
FIG. 2 illustrates an embodiment of the instrument for bending a rod including a latch for facilitating selective advancement of the rod relative to the instrument according to an embodiment of the invention.
Figure 3A:
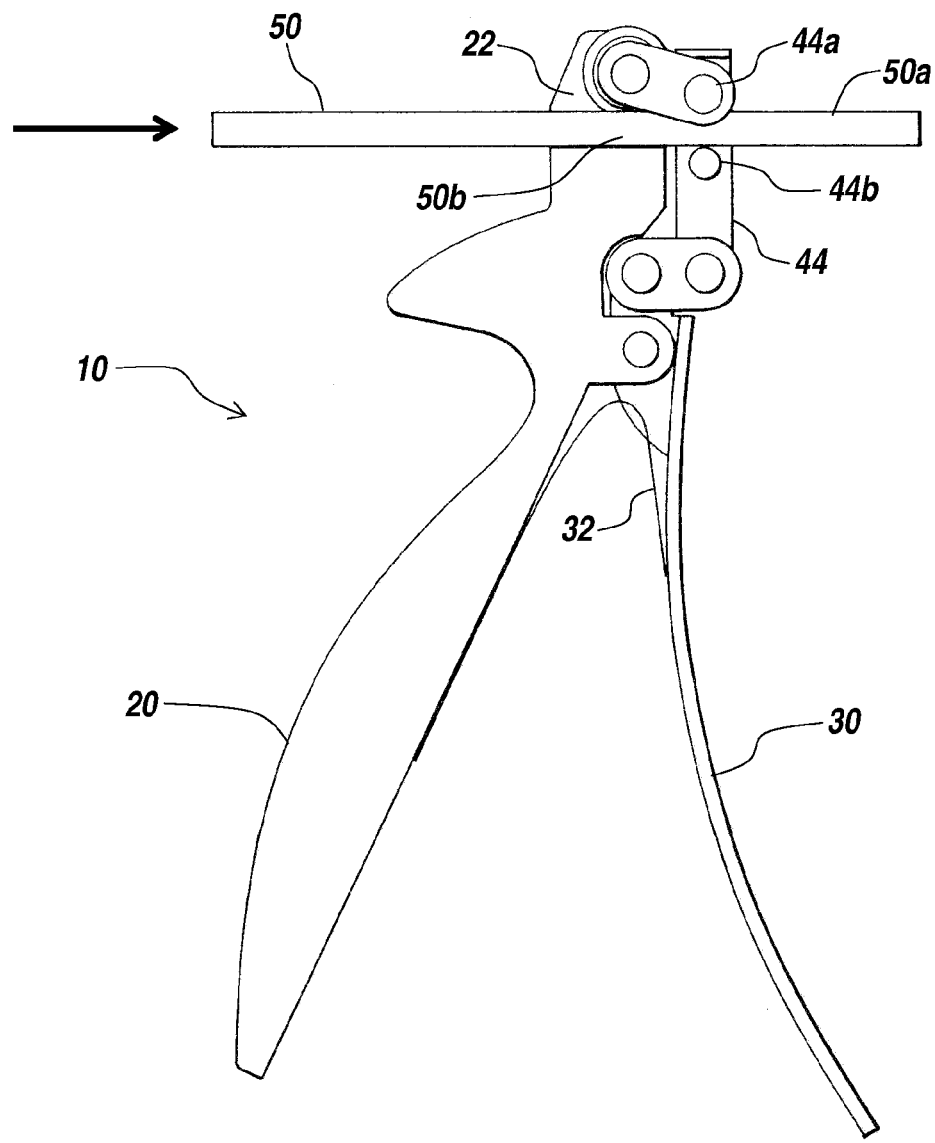
FIGS. 3A-3E illustrate the instrument of FIGS. 1A and 1B during the process of using the instrument to bend a spinal rod.
Figure 3B:
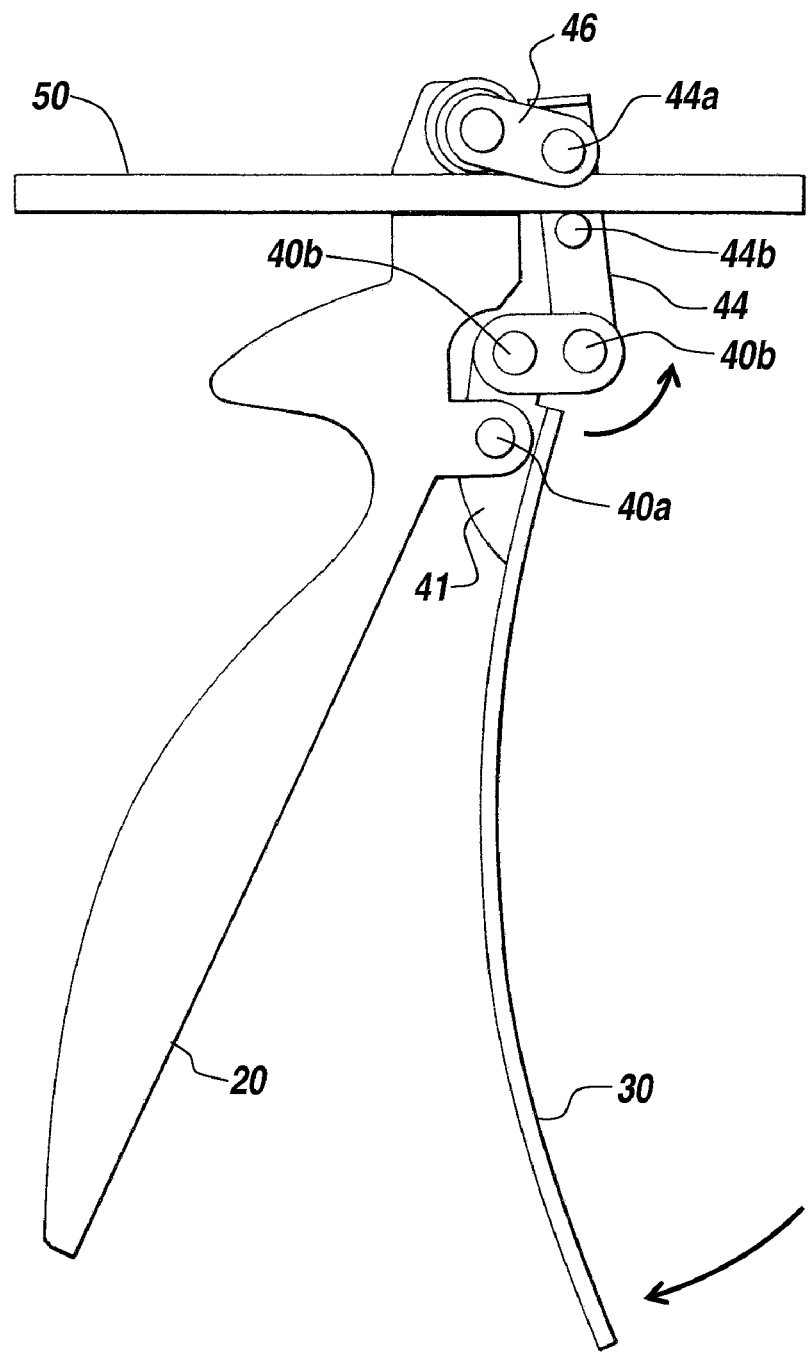
Figure 3C:
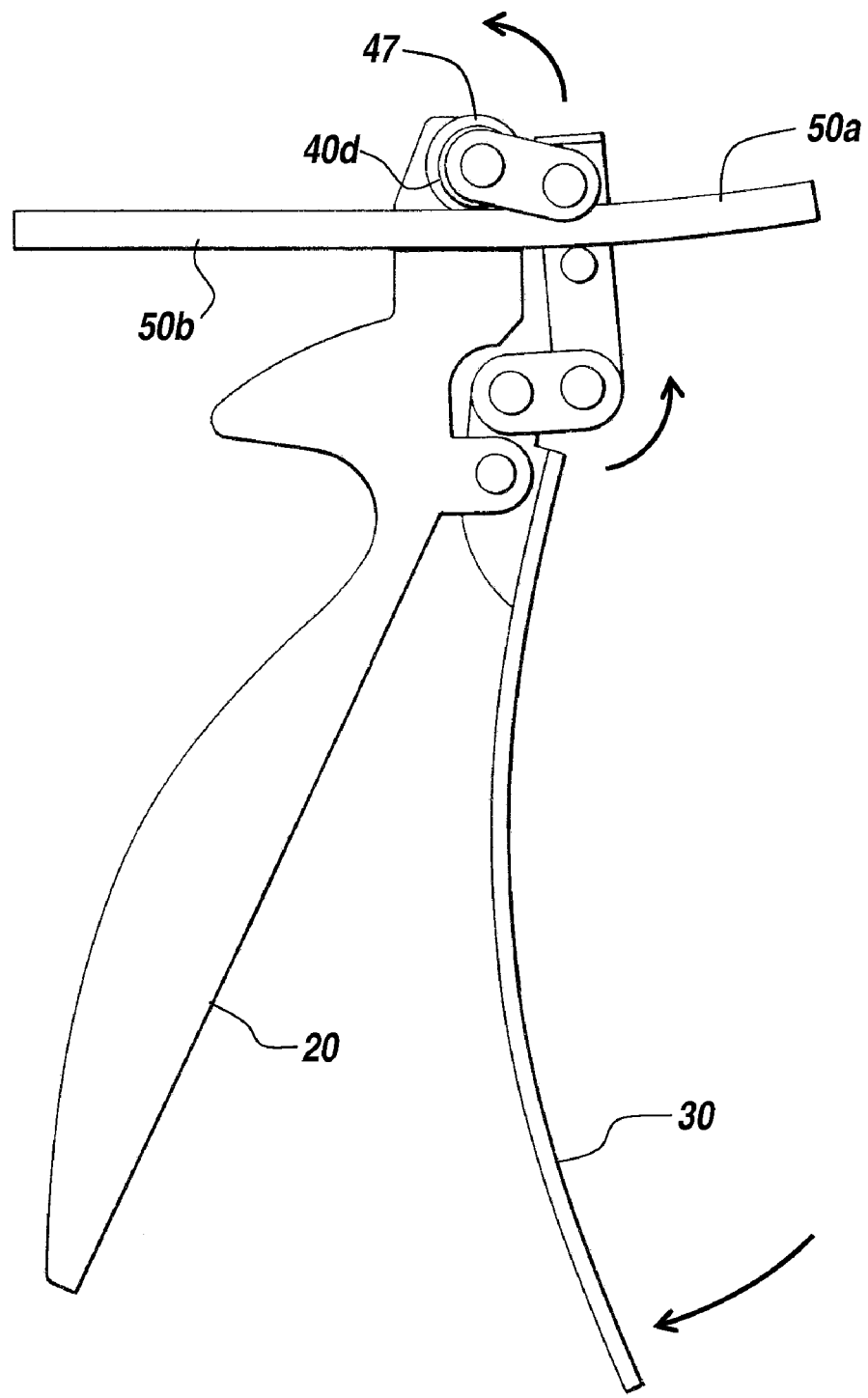
Figure 3D:
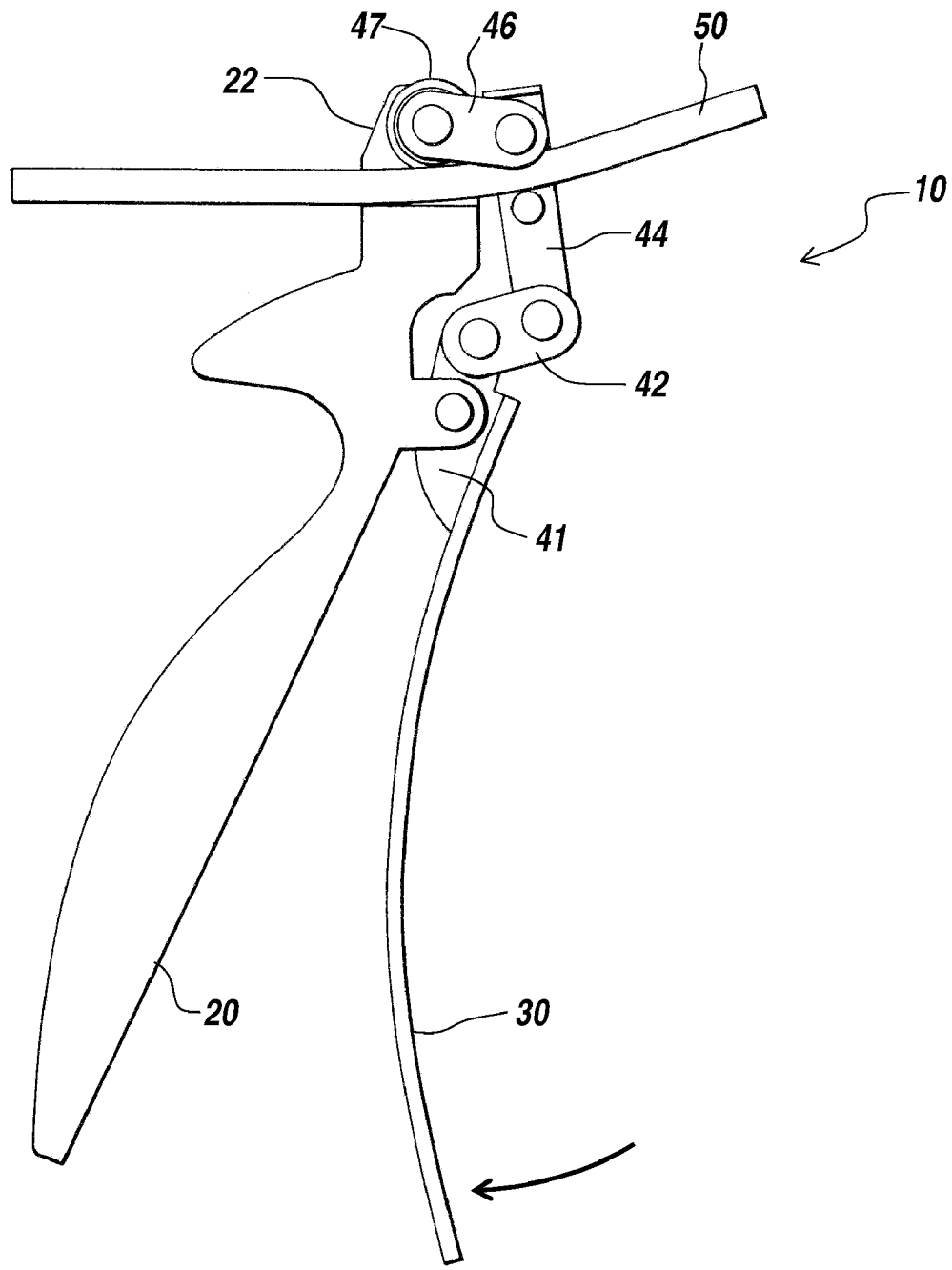
Figure 3E:
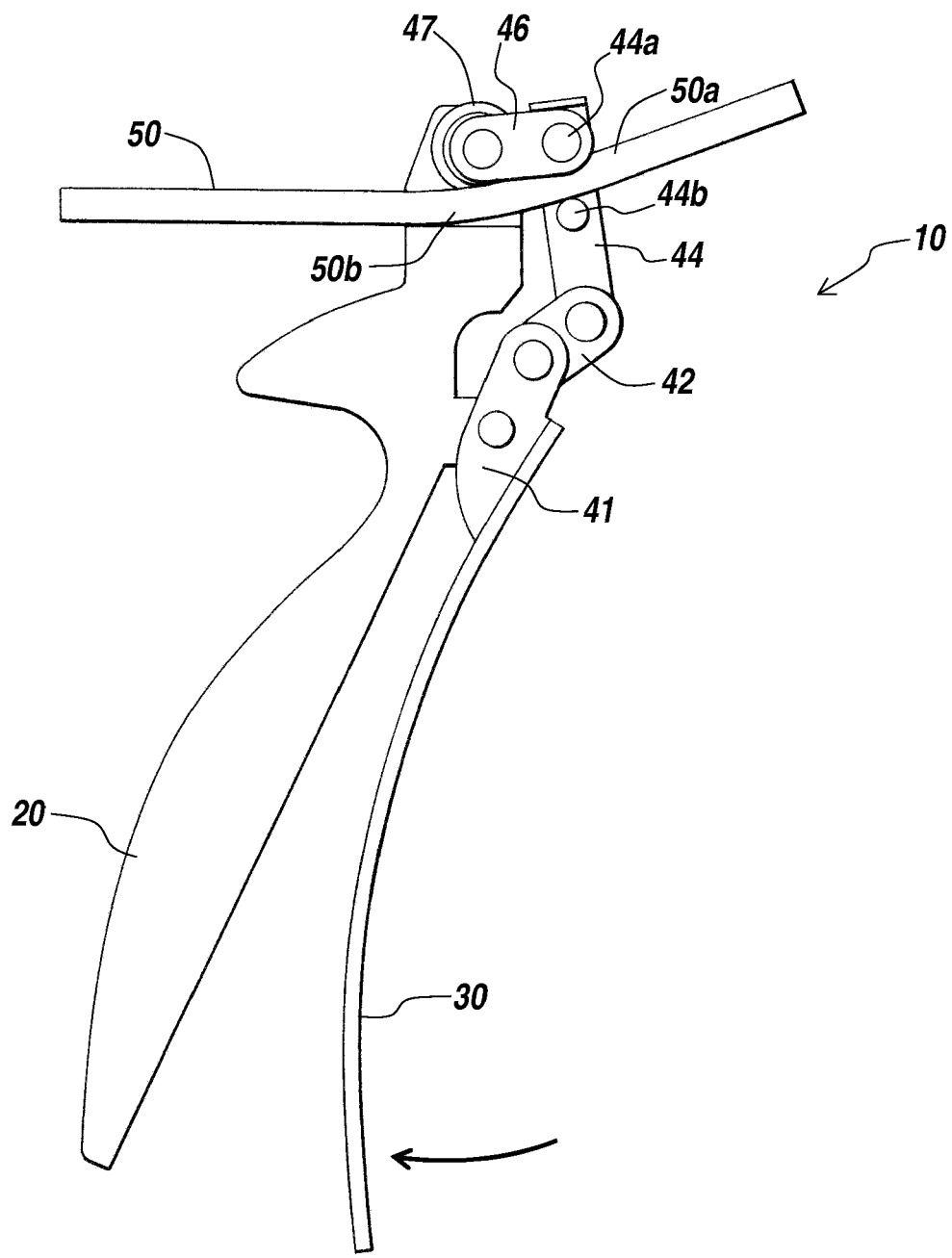

In one embodiment, shown in FIG. 2, the instrument 10 for bending a rod includes a pawl 62. As the rod advances relative to the instrument 10, the pawl 62 can latch onto the rod 50 and hold the rod in place within the channels 210, 220 until the next actuation. The illustrative pawl 62 can rotate about a pivot point 63 to facilitate retention of the rod 50.

In another embodiment, the rod advancement mechanism 60 can be a roller or other actuator which advances the rod incrementally, either when the handles are squeezed or else during the return stroke.

The lever 30 can serve as a trigger for the rod advancer 60, such that each movement of the lever 30 towards and/or away from the handle causes the rod advancer 60 to advance the rod by a predetermined amount. In an illustrative embodiment, the rod advancer advances the rod through the channels 210, 220 every time the lever 30 is moved towards the handle to create a bend, and the release of the lever maintains the rod in the advanced position after creation of the bend. The return spring 32 may reset the action of the pawl or other component holding the rod in the forward, or advanced, position. Subsequent bending iterations will then further advance the rod forward. Alternatively, the rod advancer may advance the rod through the channels 210, 220 when the lever 30 returns to a rest position, for example after a user releases the lever 30 after creating a bend. In this manner, the instrument automatically advances the rod after the instrument creates a bend in the rod to place a new, unbent portion between the rollers 44a, 44b. The user can also trigger the rod advancer without creating a bend in the rod by moving the lever 30 to an intermediate position toward the handle 20 without applying force to the rod, and releasing the lever 30 to trigger the rod advancer 60.

According to one embodiment, the rod advancer can advance the rod by a uniform amount with each actuation.

Alternatively, a user can control the amount of advancement, for example, by controlling the amount of movement of the lever 30.

The rod advancer 60 can also provide a feedback mechanism to a user regarding the amount of advancement. For example, the advancement mechanism can provide a visual or audible signal, such as a "click", to indicate to the user that the rod has advanced by a selected amount. Each "click" can correspond to a selected distance, facilitating control of the advancement. For example, a user can actuate the advancement mechanism by three clicks, bend the rod by a selected amount, then advance the rod by two clicks and bend the rod by a selected amount in order to achieve a selected bend.

Figure 1B:
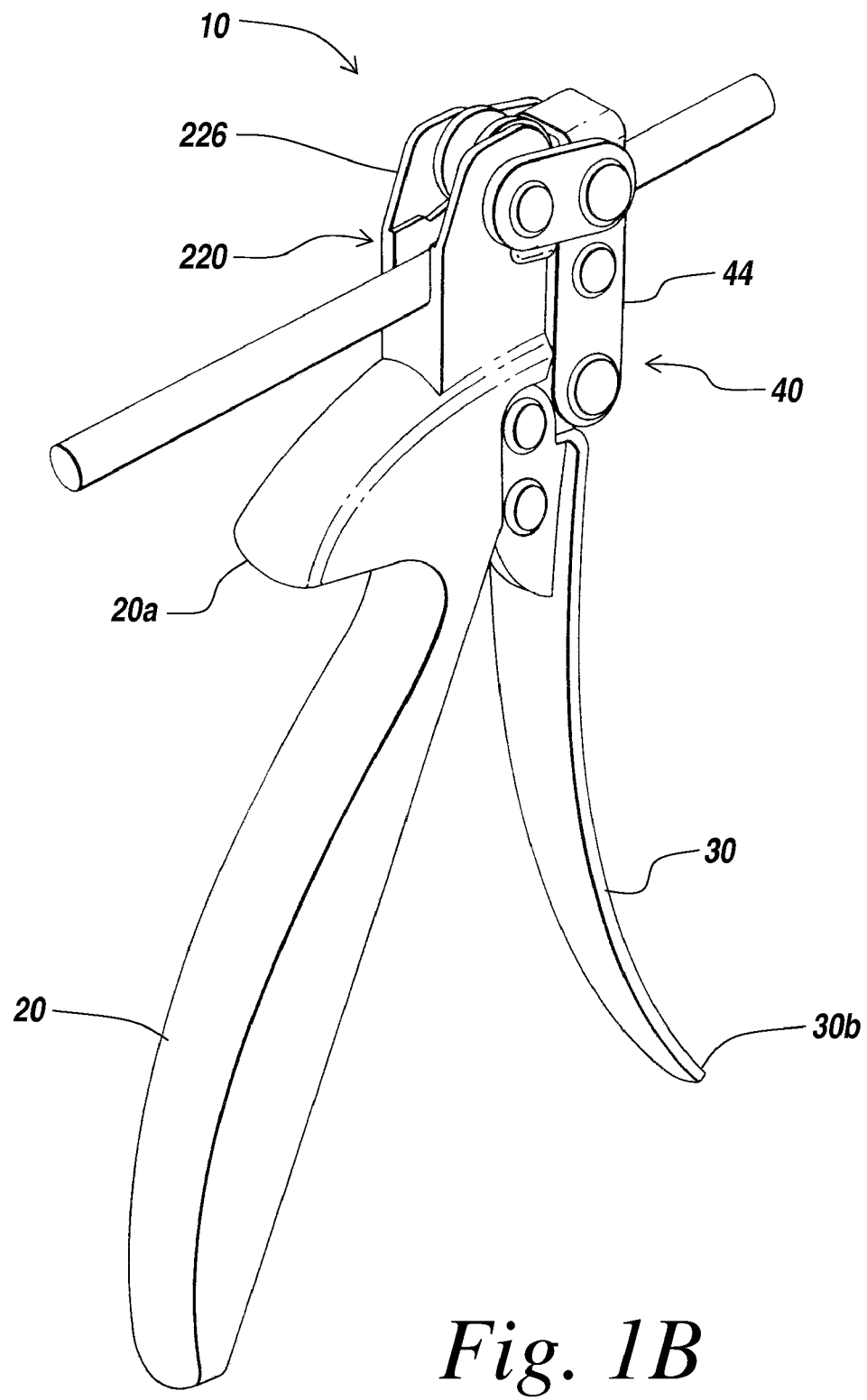
FIG. 1B is a rear perspective view of the instrument of FIG. 1A.

One skilled in the art will recognize that the components of the rod-bending instrument 10 are not limited to the embodiments shown in FIGS. 1A and 1B and that the handle 20, lever 30 and movable linkage system 40 may have any configuration suitable for bending a rod or other surgical implant.

Figure 4:
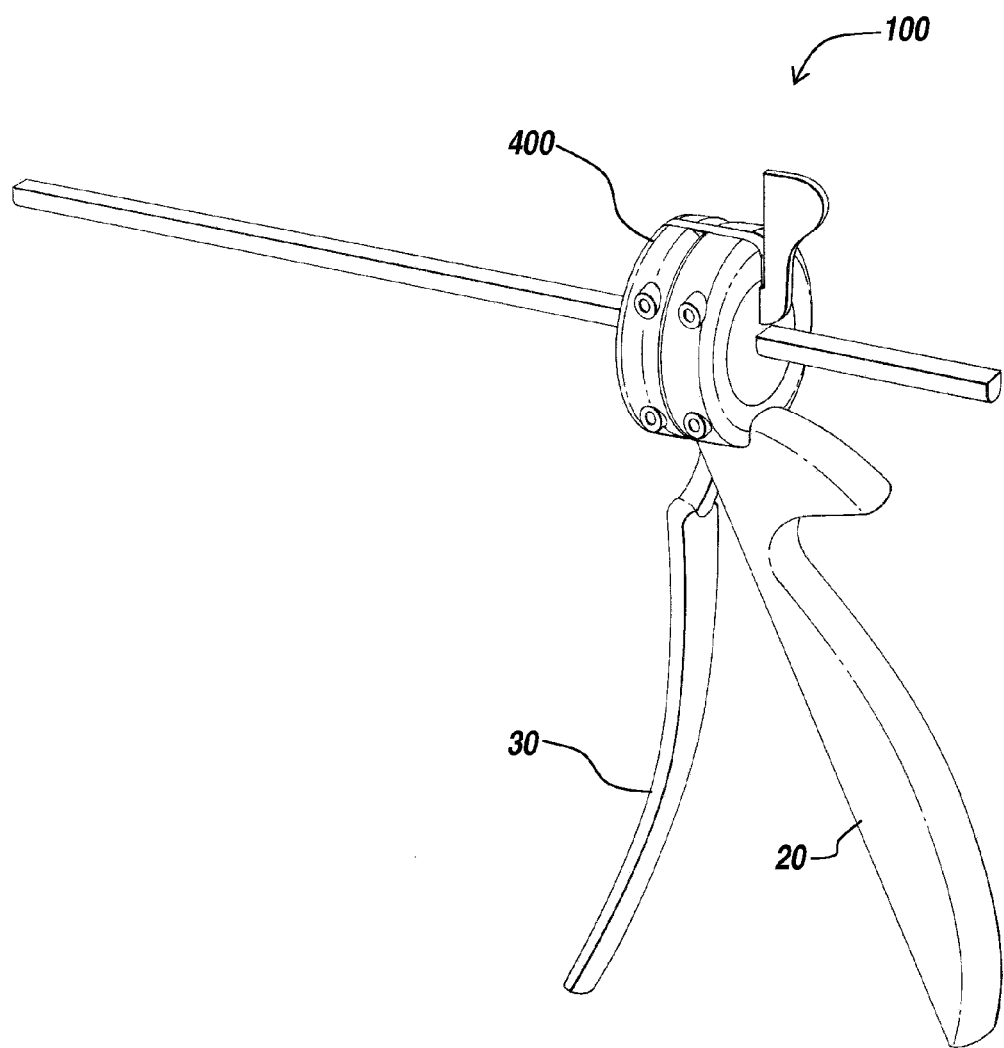
FIG. 4 illustrate an instrument for bending a rod that may have a non-circular cross section according to another embodiment of the invention.

FIG. 3 is a flow chart illustrating the steps involved in using the instrument 10 to bend a spinal rod into a selected form according to an illustrative embodiment of the invention. FIGS. 4A-4E illustrate the operation of the instrument 10 during the different steps diagrammed in FIG. 2. To use the instrument 10 to bend a rod, the user first inserts a spinal rod 50 into a selected position in the instrument in step 310. In the illustrative embodiment, the step of inserting the spinal rod 50 involves inserting the rod 50 through the rod seat 22 in step 310 and between the rollers 44a, 44b, such that a selected first portion 50a of the rod that is to be bent rests between the top roller 44a and the bottom roller 44b, and a second portion 50b is seated in the channel 220 as shown in FIG. 4A. The bend is created between the first portion 50a and the second portion 50b of the rod, in such that the first portion 50a extends at a predetermined upward angle relative to the second portion.

The rod is oriented within the channels 220, 210 such that the plane in which the rod is to be bent aligns with the plane in which the instrument causes bending. If the rod has a substantially circular cross-section, the user can rotate the rod within the channels 220, 210 until the rod 50 has a proper angular position.

After inserting the rod 50, the user triggers the instrument 10 by bringing the lower end 30b of the lever 30 towards the handle 20 in step 320. In an illustrative embodiment, the user can trigger the instrument by holding the handle 20 in the palm of one hand with the fingers of the hand resting on the lever 30 and squeezing the hand. FIG. 4B illustrates the position of the different components of the instrument during the initial movement of the lever 30 towards the handle 20. During the initial movement, the lever 30 pivots about the first pin 40a, rotating the top end 41a of lever pivot 41 about the first pin 40a, away from the handle 20, opposite the lower end 30b of the lever 30. The compound lever link 42 translates the initial movement of the top end 41a of the lever pivot 41 to the strap 44, applying a force to the strap 44 to push the strap 44 away from the handle 20. While the user squeezes the lever portion 30, the top link 46, which is attached to the handle portion 20, restrains the top end 44a of the strap 44, while the forward movement of the lever link 42 causes the strap 44 to rotate about the pin 40d into an inclined position. The rotational movement of the strap 44 about the pin 44d shifts the rollers 44a, 44b relative to the rod support 22, causing the rollers 44a, 44b to bind and tighten around the rod 50, locking the rod 50 to the strap 44.

To create a bend in the rod, the user continues to move the lower end of the lever 30 in step 330 to apply a force to the first portion 50a of the rod 50. According to an illustrative embodiment, the continued movement of the lever 30, after the rollers 44a, 44b bind the rod in step 320, forces the strap 44 to move vertically, pivoting about the pin 40d. In the illustrative embodiment, the pin 40d aligns with the top roller 44a, such that the strap 44 rotates about the top roller 44a in step 330. The rotation of the strap 44 in step 330 causes the lower roller 44b to pivot forward and up relative to the upper roller 44a, drawing the rod forward and forcing the rod against the bending roller 47, which applies a force to the top surface of the second portion 50b to prevent second portion of the rod from moving upwards with the first portion 50a. The force on the rod causes the first portion 50a of the rod between the rollers 44a, 44b to bend relative to the second portion 50b of the rod seated in the rod seat 22, as shown in FIG. 4C. As shown, the instrument 10 creates a bend in one plane, such that the first portion 50a of the rod 50 extends at a vertical angle relative to the second portion 50b of the rod.

The user continues to move the lever 30 toward the handle 20 until a desired degree of bending of the rod is reached. The user can control the vertical movement of the strap 44 and resulting degree of bend in the rod by controlling the movement of the lever 30. For example, as shown in FIG. 4D, continued movement of the lever towards the handle 20 causes the strap 44 to continue to move vertically, applying additional force to the rod 50 and providing additional bending of the rod in the selected region. In a fully compressed position, shown in FIG. 3E, the illustrative instrument 10 bends the rod 10 by about thirty degrees in a selected plane, though one skilled in the art will recognize that the invention is not limited to the illustrative embodiment and that the instrument 10 can be designed to provide any suitable degree of bending or bending of a surgical implant. The user can bend the rod in the selected location by any suitable degree by controlling the amount of movement of the lever 30.

The instrument 10 can include a feedback mechanism providing feedback to a user regarding the amount of bending occurring in the rod. In one embodiment, the feedback mechanism can comprise a ratcheting mechanism coupled to the handle that provides tactile and visual feedback to a user in the form of a "click" each time the instrument bends the rod by a selected increment. The feedback mechanism allows a user to control the bend formed in the rod. For example, the user can create a sharp bend by squeezing the lever until several clicks are heard, or a gradual bend by squeezing the lever until a single click is heard. The feedback mechanism ensures a reproducible uniform, constant curve.

For example, as shown in FIGS. 5A-5B and 6A-6F, a feedback mechanism 80 can comprise an extension 82 between the handle 20 and the lever 30 that is incrementally marked to allow the user to visualize the amount of movement of the lever 30 relative to the handle 20 to determine the degree of bending. The extension 82 may include a slot 84 configured to cooperate with a protrusion 86 that slides through the slot 84 as the lever pivots towards the handle. Incremental markings 88 on the extension 82 may be protrusions forming slots 89a, 89b, 89c, and so on, for receiving and selectively retaining the lever in a compressed position when the user releases the lever, as shown in FIGS. 6A-6F.

After bending the selected portion of the rod 50 by a predetermined amount, the user releases the handle in step 340 to terminate the application of force to the rod. According to the illustrative embodiment, the return spring 32 returns the lever to the rest position, while a strap return spring returns the strap to a rest position.

After release of the lever in step 340, the instrument 10 can automatically advance the rod 50 through the channels 210, 220 in step 350, to bring another portion of the rod into the channel 210 between the rollers 44a, 44b and another portion of the rod into the rod seat channel 220. If desired, the user can repeat steps 320-340 on the advanced portion of the rod to bend the forwarded portion of the rod by a controlled amount.

The instrument can also be used to create a two- or three-dimensional curve in the rod, if desired. The user can optionally create a two- or three-dimensional curve by rotating the rod about the longitudinal axis by a predetermined degree in an optional step 360, and repeating steps 320-340 to create a bend in the rod along a different place. The ability to create bends in the rod in multiple planes, for example, to create a two- or three-dimensional curve, allows the instrument to more accurately reproduce the contour of the spine.

Alternatively, the user can advance the rod 50 through the channels 210, 220 without bending certain intermediate portions of the rod by eliminating step 330 and releasing the lever prior to applying sufficient force to create a bend in the rod. The user can advance the rod through the instrument until a particular portion of the rod where a bend is to be made rests between the channels 210 and 220.

The rod-bending instrument 10 of the present invention provides significant advantages over the prior art. The instrument is ergonomically sound, provides greater control over the degree and orientation of bending, and provides greater mechanical advantage to the user. Unintentional out of plane bending is minimized, which the instrument facilitates intentional two-dimensional or three-dimensional bends. The use of a plurality of hinge points to translate a movement of the lever to a component that applies force to bend a rod provides a significant mechanical advantage, allowing the user to create one or more controlled bends in a rod without applying a strenuous amount of force. For example, design of the strap 44 provides additional mechanical advantage to the instrument 10, because of the difference between the length of the lower end of the strap relative to the restrained rod 50 the upper end 442 being restrained by the top link. The instrument can also be used with a single hand, further facilitating use.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. An instrument for bending a surgical implant, comprising:
   a handle including a rod seat for receiving a first portion of the surgical instrument;
   a lever pivotally connected to the handle; and
   a movable linkage system including a plurality of pivotally connected links for pivotally connecting the lever to the handle, wherein one of said pivotally connected links applies a force to the surgical implant to bend a second portion relative to the first portion upon pivoting the lever relative to the handle.

2. The instrument of claim 1, wherein the lever includes a first end, a second end and a pivot point located in the vicinity of the first end for rotating the second end relative to the handle.

3. The instrument of claim 2, wherein the movable linkage system comprises a lever pivot connected to the first end of the lever, a compound lever link having a first end pivotally connected to the lever pivot and a strap pivotally connected to a second end of the compound lever link and defining a channel for receiving the second portion of the surgical instrument,
   wherein movement of a second end of the lever towards the handle pushes the lever pivot and compound lever link away from the handle, causing the strap to apply a force to the surgical implant.

4. The instrument of claim 3, wherein the strap includes a top roller and a bottom roller defining the channel and including bearing surfaces for applying a force to the surgical implant.

5. The instrument of claim 3, further comprising a top link having a first end pivotally connected to the handle and a second end pivotally connected to the strap for constraining the movement of the strap.

6. The instrument of claim 5, wherein the strap pivots with the top link to displace the channel relative to the first portion of the implant, thereby applying a force to the surgical implant.

7. The instrument of claim 6, further comprising a bending roller coupled to the first end of the top link for securing the first portion of the surgical implant to a rod seat coupled to the handle and applying a force to bend the second portion of the surgical implant when the strap pivots with the top link.

8. The instrument of claim 1, further comprising an advancement mechanism for automatically advancing the surgical implant relative to the instrument.

9. The instrument of claim 1, further comprising a spring for biasing the lever away from the handle.

10. The instrument of claim 1, further comprising a rotatable insert defining a first channel for receiving said first portion and a second channel for receiving the second portion, the insert adapted for selectively rotating the surgical implant relative to the handle and lever.

11. The instrument of claim 10, wherein the first channel and second channel are sized and configured to receive a spinal rod.

12. An instrument for bending a surgical implant, comprising:
   a handle;
   a lever pivotally connected to the handle;
   a movable linkage system pivotally connecting the lever to the handle and applying a force to bend a first portion of the surgical implant relative to a second portion of the surgical implant upon pivoting the lever relative to the handle; and
   an advancement mechanism for moving the surgical implant relative to the instrument upon pivoting of the lever relative to the handle.

13. The instrument of claim 12, wherein the lever pivots towards the handle to create a bend and to actuate the advancement mechanism.

14. The instrument of claim 12, wherein the lever pivots towards the handle to create a bend and away from the handle to actuate the advancement mechanism.

15. An instrument for bending a spinal rod, comprising:
   a handle having a first end and a second end,
   a rod seat connected to the first end of the handle for receiving a first portion of the spinal rod;
   a bending roller coupled to the rod seat and defining a top portion of the rod seat;
   a lever pivotally connected to the handle at a pivot point between the first end and the second end of the handle, the lever having a first end and a second end, the pivot point being located between the first end and the second end of the lever; and a movable linkage system coupled to the first end of the lever and said bending roller for applying a force to a second portion of the rod to bend the second portion of the rod relative to the first portion upon movement of the second end of the lever towards the second end of the handle.

16. The instrument of claim 15, wherein the pivot point is closer to the first end of the lever than the second end of the lever.

17. The instrument of claim 15, wherein the movable linkage system comprises a plurality of pivotally connected links, one of said links including a pair of rollers defining a channel for receiving the second portion of the rod, wherein said rollers bend the second portion of the rod about the bending roller when a user moves the second end of the lever towards the second end of the handle.

18. The instrument of claim 17, wherein said link including the pair of rollers pivots about one of said rollers when the user moves the second end of the lever to apply the force to the rod.

19. The instrument of claim 15, further comprising an advancement mechanism for automatically advancing the rod in the rod seat.

* * * * *